United States Patent [19]

Saint Just et al.

[11] Patent Number: 5,200,376
[45] Date of Patent: Apr. 6, 1993

[54] CATALYSTS FOR OXYHYDROCHLORINATION OF METHANE

[75] Inventors: Jacques Saint Just, Le Pecq; Yaounès B. Taarit, Tassin La Demi Lune; Meyer C. Naccache, Ecully; Michel Dufaux, Saint Germain Mont D'or, all of France

[73] Assignee: Gaz De France, France

[21] Appl. No.: 690,497

[22] Filed: Apr. 24, 1991

[30] Foreign Application Priority Data

Apr. 27, 1990 [FR] France ................................ 90 05454

[51] Int. Cl.$^5$ ............................................. B01J 29/04
[52] U.S. Cl. ....................................... 502/60; 502/64; 502/77; 502/78; 502/79; 570/243
[58] Field of Search ................... 423/328; 502/79, 78, 502/77, 60, 64, 244; 570/243

[56] References Cited

U.S. PATENT DOCUMENTS

| | | | |
|---|---|---|---|
| 3,346,328 | 10/1967 | Sergeys et al. | 502/79 |
| 3,649,177 | 3/1972 | Rosback | 502/79 |
| 3,987,118 | 10/1976 | Kuck | 570/224 |
| 4,123,389 | 10/1978 | Pieters et al. | 502/225 |
| 4,814,527 | 3/1989 | Diesen | 570/243 |
| 4,911,899 | 3/1990 | Hagiwara et al. | 423/328 |

FOREIGN PATENT DOCUMENTS

| | | | |
|---|---|---|---|
| 1172002 | 11/1969 | United Kingdom | 502/79 |
| 1222249 | 2/1971 | United Kingdom | |
| 2095243 | 9/1982 | United Kingdom | |

OTHER PUBLICATIONS

Iwamoto et al. "Evidence for the Presence of Extra Framework Oxygen Species in Partially Metal-Ion-Exchanged y Zeolites" J. Phys. Chem. 86(2) 1982 pp. 153-156.

Iwamoto et al. "Discrimination of Reduction Processes of Partially Cupric Ion-Exchanged Y Zeolites by a Temperature-Programmed Reduction Technique" Chem. Letters 1983 pp. 471-472.

Bhatt et al. "Infrared & Thermal Studies of Interaction of Pyridine and Triethanolamine with Partially Copper (11)-exchanged Zeolite AW500" Indian J. Chem. 19A (1980) pp. 472-473.

Iwamoto et al. "Exchange of Oxygen between Water and a Partially Copper (11)-Exchanged Y Zeolite" J. Phys. Chem. 85(26) 1981, pp. 3954-3957.

Bandiera et al. "Propriétés Catalytiques des Zeolithes Nay Partiellement Échangées par des Ions Cu$^{2+}$ et Différemment Activées Vis-a-Vis de la Migration de la Double Liaison du 1-Butène" J. Chim. Phys. 70(7-8) 1973 pp. 1096-1101.

Bandiera et al. "Catalyse" C.R. Acad. Sc. Paris Ser. C 282, 1976 pp. 81-84.

Burton et al. "Nitric Oxide Reduction with Ammonia over Cu(11) Y Zeolites" J. Phys. Chem. 80(24) 1976 pp. 2664-2671.

Schoonheydt et al. "Conduction and Relaxation of Cations in Dehydrated Partially Copper (11)-exchanged Synthetic Faujasites" J. Chem. Soc. Faraday Trans. 1 72(1) 1976 pp. 172-183.

Tabourier et al. "Physique des Solides" C.R. Acad. Sc. Paris, 284 Ser. B (1977) pp. 107-109.

Namba et al. "Shape-Selective Disproportionation of Xylene over Partially Cation-Exchanged H-Mordenite" J. Cat. 56 (1979) pp. 445-452.

*Primary Examiner*—R. Bruce Breneman
*Attorney, Agent, or Firm*—Ostrolenk, Faber, Gerb & Soffen

[57] ABSTRACT

Catalysts for the oxyhydrochlorination of methane into methyl chloride, comprising a chemical compound of great specific surface area of the zeolite type which is partially exchanged at least with divalent metallic cations, preferably Cu$^{++}$ cations, the catalysts being applicable in particular to the formation of monochlorinated products usable as such or as intermediate chemical agents.

4 Claims, 1 Drawing Sheet

CATALYSTS FOR OXYHYDROCHLORINATION OF METHANE

BACKGROUND OF THE INVENTION

1. Field of the Invention

The present invention relates to new catalysts for the oxyhydrochlorination of methane into methyl chloride.

2. Description of the Related Art

The oxyhydrochlorination is a well-known chemical reaction which consists in making light alkanes react with hydrogen chloride and oxygen in the presence of a catalyst for obtaining chlorinated products. Thus, the oxyhydrochlorination of methane for the production of methyl chloride takes place according to the following reaction principle:

$$CH_4 + HCl + \tfrac{1}{2}O_2 \xrightarrow{catalyst} CH_3Cl + H_2O.$$

The U.S. Pat. No. 4,123,389 in particular discloses the oxyhydrochlorination of methane by using a catalyst consisting of a silicon oxide, titanium oxide or alumina α carrier or support with a high specific surface area onto which are deposited copper chlorides, essentially cuprous chlorides, alkaline metal chlorides (KCl) and rare earths chlorides (LaCl$_3$).

Studies have however shown that if this kind of catalyst exhibits a rather good activity and selectivity, it is unstable and would easily become decomposed upon an extended use. Moreover, the preparation of this catalyst requires harsh precautions as to the prohibition of use of water and requires a strict experimental scheme difficult to be complied with.

SUMMARY OF THE INVENTION

Thus an object of the present invention is to provide new catalysts for oxyhydrochlorination which exhibit a good activity and selectivity, which are chemically stable upon an extended use and which moreover do not require harsh precautions for their preparation and use.

The catalysts for the oxyhydrochlorination of methane into methyl chloride according to the present invention comprise a chemical compound of great specific surface area of the zeolite type which is partially exchanged at least with divalent metallic cations, preferably Cu$^{++}$ cations.

According to further characterizing features of the catalysts of the present invention, the zeolite preferably is a zeolite of the Y-type which in the initial state meets the general formula Na$_{56}$(AlO$_2$)$_{56}$(SiO$_2$)$_{136}$.

The exchanged zeolite comprises between about 0.5 and 10% by weight of Cu$^{++}$ cations, preferably between about 0.5 and 7.6% by weight and more preferentially 4.6% by weight of Cu$^{++}$ cations.

The zeolite is moreover exchanged with Mn$^{++}$ cations; and

The exchanged zeolite comprises about 2% by weight of Mn$^{++}$ cations.

Another subject of the invention is a method for the oxyhydrochlorination of methane into methyl chloride which consists in using a specific catalyst.

BRIEF DESCRIPTION OF THE DRAWINGS

Further objects, details, characterizing features and advantages of the present invention will appear more clearly when reading the following detailed explanatory description with reference to the accompanying diagrammatic drawings given by way of non limiting examples only illustrating several embodiments of the invention and wherein.

DESCRIPTION OF THE PREFERRED EMBODIMENT

Figure 2:
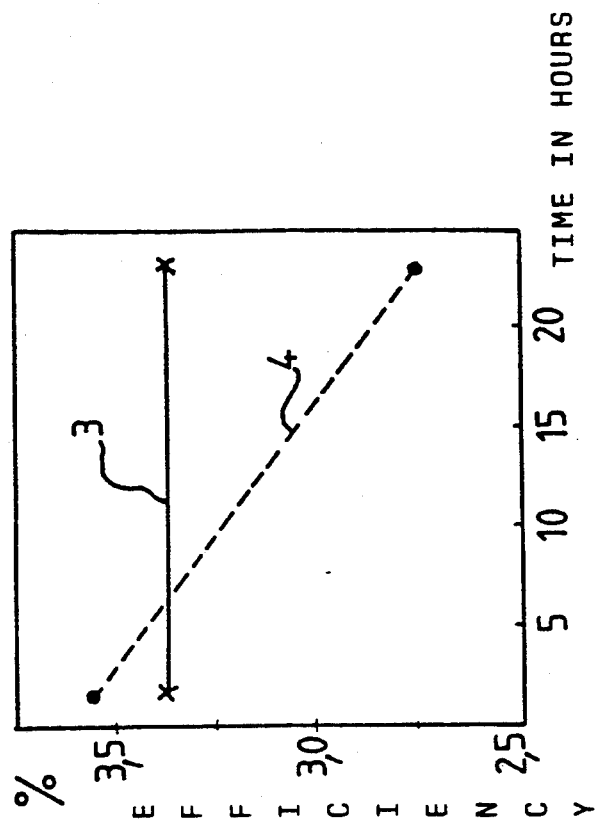
FIG. 2 shows the variation of the efficiency in percentage of a catalyst 3 of the present invention and of a prior art catalyst 4 versus time.

The zeolites are alumino-silicates of the general formula Na$_{56}$(AlO$_2$)$_{56}$(SiO$_2$)$_{136}$. The sodium and aluminium atoms are present in the same number so as to provide for the electrical neutrality of the whole. It is possible to vary the ratio Si/Al and to replace the Na$^+$ cations by other cations such for instance as copper (Cu$^{2+}$) so as to obtain an exchanged zeolite meeting the formula Na$_{56-x}$Cu$_{x/2}$(AlO$_2$)$_{56}$(SiO$_2$)$_{136}$ wherein x stands for the number of exchanged atoms in the elementary link.

Several types of zeolites have been exchanged according to the process described hereinabove and the catalysts thus obtained have been tested for providing a comparison of their performances.

The results are summarized in tables I and II hereinafter.

Preparation of the catalysts.

A given mass of zeolite is contacted with a required computed amount of a solution, for example 1 M of copper sulphate or nitrate providing for the desired exchange rate. With small exchange rates down to 15%, the contact may be made in one single time. The zeolite is stirred in a solution at room temperature for about 8 hours. The discoloring of the solution and the coloring of the solid upon decanting are noticed. The separation may indifferently be made through centrifugation or filtration. The separation is followed by several washings with deionized water. The final washing should be very meticulous and it should be made sure for instance that the washing waters do no longer contain any SO$_4^{2-}$ or NO$_3^-$ ions.

Comparison of the performances of various catalysts.

Five types of zeolite have been prepared according to the process described hereinabove and have been tested as catalysts. The reaction is effected at atmospheric pressure every 20° C. between 300° and 440° C. and to compare the catalysts the following conditions have been adopted:

Total flow rate: 8 l/h with helium as a carrier gas; $P_{O2} = P_{HCL} = P_{CH4} = 12.66$ kPa.

The results are summarized in tables I and II hereinafter and are given for two reference temperatures: 360° C. and 400° C.

TABLE I

| | reaction at 360° C. | |
|---|---|---|
| Solids | CH$_3$Cl m.moles h$^{-1}$ g$^{-1}$ | CO m.moles h$^{-1}$ g$^{-1}$ |
| YNa/Cu 4.6% | 1.7 | 0 |
| LNa/Cu 3% | 1.0 | 0 |
| ZSM5/Cu 2% | 1.0 | 0 |
| Mordenite Na/Cu 2% | 0.24 | 0 |
| XNa/Cu 3% | 0.14 | 0 |

TABLE II

| | reaction at 400° C. | |
|---|---|---|
| Solids | CH$_3$Cl<br>m.moles h$^{-1}$ g$^{-1}$ | CO<br>m.moles h$^{-1}$ g$^{-1}$ |
| YNa/Cu 4.6% | 4.2 (57%) | 3.2 (43%) |
| LNa/Cu 3% | 3.4 (60%) | 2.3 (40%) |
| ZSM5/Cu 2% | 2.3 (72%) | 0.9 (28%) |
| Mordenite Na/Cu 2% | 1.8 (55%) | 1.5 (45%) |
| XNa/Cu 3% | 0.6 (67%) | 0.3 (33%) |

As it appears from the above tables the Y-zeolite exhibits the best performances but is however less selective than other zeolites at the temperature of 400° C.

The production of CO may be ascribed to a secondary oxidation of one portion of the methyl chloride produced.

Influence of the copper content upon the catalysts of the invention.

Various catalysts of the present invention have been prepared by exchanging a NaYzeolite with Cu$^{2+}$ cations as previously described and by varying the Cu$^{2+}$ content in the NaYzeolite. The catalysts thus obtained have been tested in order to determine their performances in a reaction of oxyhydrochlorination of methane.

The tests have been run with a reactor with an internal diameter of 1.2 cm. with a height of powder catalyst column of 1.5 cm for a used available maximum mass of catalyst of 0.680 g.

Each reaction has been carried out at a temperature of 342° C. and according to the following conditions:

| Pressures: | CH$_4$: | 33.72 kPa |
|---|---|---|
| | O$_2$: | 16.89 kPa |
| | HCl: | 16.89 kPa |
| | He: | 33.72 kPa |
| | total: | 101.30 kPa |
| | CH$_4$/O$_2$ = CH$_4$/HCl = 2 | |
| Flow rates: | CH$_4$: | 1 l/h |
| | O$_2$: | 0.5 l/h |
| | HCl: | 0.5 l/h |
| | He: | 1 l/h |
| | total: | 3 l/h |

The results of theses tests have been shown in table III hereinafter:

TABLE III

| | | | | | | | Conv. % | |
|---|---|---|---|---|---|---|---|---|
| Y Na % Cu | P$_{CH_3Cl}$/g cata | Selectivity in CH$_3$Cl, % | P$_{CO}$/g cata | Selectivity in CO, % | P$_{CO_2}$/g cata | Selectivity in CO$_2$, % | CH$_4$/g cata | HCl/g cata |
| 0.5 | 5.4 | 100 | — | — | — | — | 2.1 | 4.25 |
| 1.0 | 6.8 | 92 | 0.6 | 8 | — | — | 2.9 | 5.35 |
| 2.1 | 7.5 | 87 | 1.1 | 13 | — | — | 3.4 | 5.9 |
| 4.6 | 8.6 | 84 | 1.6 | 16 | — | — | 4.0 | 6.77 |
| 7.6 | 6.6 | 84 | 1.3 | 16 | — | — | 3.1 | 5.2 | cata = catalyst
P = pressure in kPa
conv. = conversion

The results summarized in the table hereinabove show that there is a compromise between activity and selectivity and that this compromise exists with a copper content of about 4% in NaY.

Comparison of catalysts of the present invention and of the prior art.

The catalyst according to the U.S. Pat. No. 4,123,389 has been tested in the same conditions of reaction of oxyhydrochlorination than those described hereinabove for the catalysts of the present invention. A comparison has been made between the catalyst of the present invention with a copper content of 4.6% by weight and the catalyst of the prior art.

The results are summarized in the table IV hereinafter:

TABLE IV

| | | Selectivity % | | | | | Conversion % per gramme of cata | |
|---|---|---|---|---|---|---|---|---|
| Catalyst | P$_{CH_3Cl}$/g cata | CH$_3$Cl | CH$_2$Cl$_2$ CHCl$_3$ CHCl$_4$ | CO | P$_{CO}$/g cata | Selectivity CO, % | CH$_4$ | HCl |
| NaYCu Cu 4.6% by weight | 8.6 | 84 | 0 | 16 | 1.6 | 16 | 4.0 | 6.8 |
| U.S. Pat. No. 4,123,389 (Example I) | 9.3 | 93 | 0 | 7 | 0.7 | 7 | 3.9 | 7.3 | cata = catalyst
P = pressure in kPa

As it appears from the table hereinabove the catalyst of the prior art appears to be initially slightly better than the catalyst of the present invention since with a substantially equal conversion rate (of the order of magnitude of 4%) it is substantially more selective in CH$_3$Cl. The initial superiority of the catalyst of the prior art however is at the best at 10%.

Comparison of the stability of the catalysts of the invention and of the prior art.

In order to determine and to compare the stability of the catalyst of the present invention and of that of the prior art, tests have been carried out after 24 hours of activity on the catalyst of the present invention and on the catalyst of the prior art, the latter having previously been regenerated according to the scheme disclosed in the U.S. Pat. No. 4,123,389.

The results obtained are summarized in table V hereinafter and on the accompanying FIGS. 1 and 2 in which the curves 1 and 3 relate to the catalyst of the present invention and the curves 2 and 4 to the catalyst of the example I of the U.S. Pat. No. 4,123,389. The efficiency or yield in percentage is the product of the activity and of the selectivity.

TABLE V

| Catalyst | $P_{CH_3Cl}$/g cata | Selectivity $CH_3Cl$, % | $P_{CO}$/g cata | Selectivity CO, % | Conversion % $CH_4$/g cata | HCl/g cata |
|---|---|---|---|---|---|---|
| NaY Cu % weight Cu: 4.6 | 8.6 | 84 | 1.6 | 16 | 4.0 | 6.8 |
| U.S. Pat. No. 4,123,389 | 5.9 | 94 | 0.4 | 6 | 2.9 | 4.96 |

P: pressure in kPa
cata: catalyst

Figure 1:
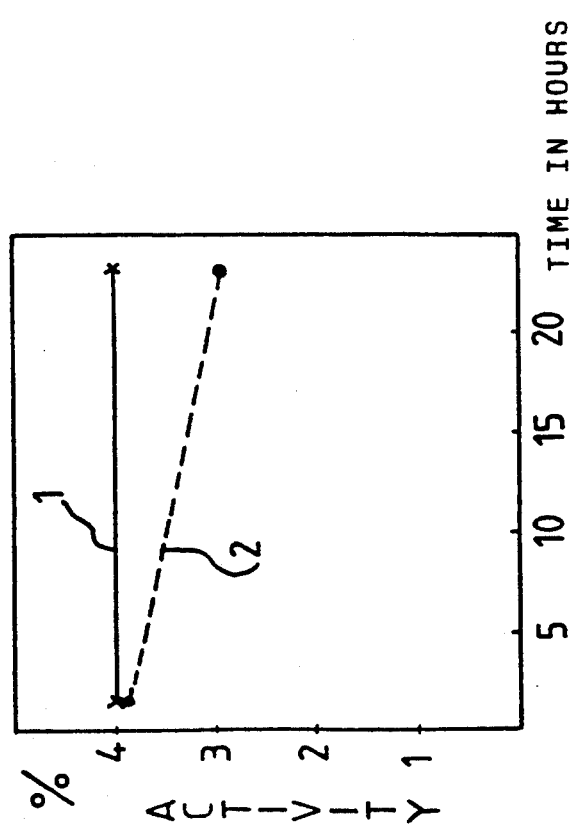
FIG. 1 graphically shows the variation in the activity expressed in percentage of a catalyst 1 according to the present invention and of a prior art catalyst 3 versus time.

As it appears from IV and V and from the accompanying FIGS. 1 and 2 after 24 hours of use the performance of the catalyst of the prior art decreases very distinctly with respect to the activity which changes from 3.9% to 2.9% with however a slight increase in the selectivity in $CH_3Cl$ which changes from 93% to 94%. This increase indeed is not significant since with respect to the partial oxidizing reactions, a decrease in conversion should result in an increase in the selectivity without the efficiency or yield of the reaction being greatly altered. In the present case, the efficiency with respect to methane passes from 3.6% to 2.7% in 24 hours, hence a drop of 25%, thereby indicating a very quick de-activation of the catalyst of the prior art. This lack of stability of the prior art catalyst is not surprising to the extent where under the conditions of reaction, the catalyst probably is in the form of a supported molten salt of $CuCl_2$ one part of which is likely to be carried along by the gas flow rate thereby involving a loss of substance.

On the contrary, the catalyst of the present invention is stable over the period of 24 hours.

The comparison of the catalysts of the prior art and of the present invention has been extended to different tests conditions. i.e. under the following conditions:

| | |
|---|---|
| Temperature | 342° C., |
| Total P | 101.30 kPa |
| $P_{CH_4}$ | 72.38 kPa |
| $P_{O_2} = P_{HCl}$ 1 | 14.43 kPa |
| $CH_{4/O_2} = CH_4HCl = 5$ (instead of 2), | |
| Total flow rate = | 7 l/h |
| catalyst mass used: | 0.680 g. |

The results are summarized in the table VI hereinafter:

TABLE VI

| Catalyst | $P_{CH_3Cl}$/g cata | Selectivity $CH_3Cl$, % | $P_{CO}$/g cata | Selectivity Co, % | Conversion % $CH_4$/g cata | HCl/g cata |
|---|---|---|---|---|---|---|
| NaYCu % by weight Cu: 4.6 | 13.8 | 90 | 1.6 | 10 | 2.8 | 12.7 |
| Catalyst U.S. Pat. No. 4,123,389 | 15.5 | 91 | 1.5 | 9 | 3.1 | 14.4 |
| NaYCu % by weight Cu: 4.6 after 24 h | 13.8 | 90 | 1.6 | 10 | 2.8 | 12.7 |
| Catalyst U.S. Pat. No. 4,123,389 after 24 h | 9.5 | 87 | 1.4 | 13 | 2.0 | 7.5 | cata = catalyst
P: pressure in kPa

Under these more reducing conditions, the prior art catalyst initially retains better performances than the catalyst of the present invention. After 24 hours of use however the selectivity of the prior art catalyst decreases with a concurrent decrease in activity whereas the catalyst of the present invention is as selective and active and therefore becomes definitely better than the prior art catalyst.

As a conclusion under the conditions considered to be more favorable to the prior art catalyst, the latter indeed is more productive by 8% in view of a better selectivity than the catalyst of the present invention. However after 24 hours of use only the catalyst of the present invention which does not undergo any de-activation becomes definitely better in terms of productivity (+31%) and of selectivity (90% against 87%).

Moreover it should be pointed out that at great conversion rates, the prior art catalyst produces chlorinated products others than methyl chloride whereas the catalyst of the present invention remains selective in methyl chloride.

At last, the catalyst of the invention are prepared merely by ionic exchange without any special precaution and do not require harsh mesures of use.

Although the catalysts of the present invention have great performances as this appears from the foregoing description, it has been attempted to still further improve their performances by changing their chemical compositions. The YNaCu Zeolite with 4.6% by weight of copper has therefore been successively doped with $Fe^{3+}$, $Ag^{2+}$ and $Mn^{2+}$ ions which have been inserted in turn through ionic exchange according to the process previously described.

The catalysts thus obtained have been tested at two temperatures of 360° C. and 400° C., respectively, under the following conditions of reaction: Total flow rate: 8 l/h with helium as a carrier gas $P_{O_2} = P_{HCl} = P_{CH_4} = 12.66$ kPa.

The results obtained are shown in tables VII et VIII hereinafter.

TABLE VII

| Catalyst | Reaction at 360° | |
|---|---|---|
| | CH$_3$Cl mmoles h$^{-1}$ g$^{-1}$ cata | CO mmoles h$^{-1}$ g$^{-1}$ cata |
| YNa/Cu 4.6% | 1.67 | — |
| YNa/Cu 4.6% + 1% Fe | 2.00 | 0.55 |
| YNa/Cu 4.6% + 3% Fe | 1.30 | 0.40 |
| YNa/Cu 4.6% + 2% Ag | 0.9 | — |
| YNa/Cu 4.6% + 2% Mn | 1.4 | — | cata: catalyst

TABLE VIII

| Catalyst | Reaction at 400° C. | |
|---|---|---|
| | CH$_3$Cl mmoles h$^{-1}$ g$^{-1}$ cata | CO mmoles h$^{-1}$ g$^{-2}$ cata |
| YNa/Cu 4.6% | 4.1 (56%) | 3.2 |
| YNa/Cu 4.6% + 1% Fe | 5.2 (47%) | 5.8 |
| YNa/Cu 4.6% + 3% Fe | 4.5 (57%) | 3.4 |
| YNa/Cu 4.6% + 2% Ag | 2.8 | 1.3 |
| YNa/Cu 4.6% + 3% Mn | 4.7 (71%) | 1.9 | cata: catalyst.

It appears from the tables hereinabove that the exchange of the Fe$^{3+}$ and Mn$^{2+}$ ions in the YNazeolite with 4.6% of copper pratically always increases the activity but that the Fe$^{3+}$ ions (from 1% to 3%) result in a drop of selectivity probably due to their favourable action for the combustion of methyl chloride whereas the Mn$^{2+}$ ions always produce an increase in selectivity. As to the Ag$^{2+}$ ions they decrease the activity but without changing the selectivity.

It may therefore be said that among the active cations the Mn$^{2+}$ cations are the best because without resulting in a decrease of the conversion rate and of the stability of the catalyst, they improve the selectivity.

Complementary tests have been run in order to establish a comparison between the basic catalyst of the present invention, the catalyst doped with the manganese and the prior art catalyst. The conditions of reaction are such as defined for the tests, the results of which are summarized in table III.

The results are shown in table IX herebelow.

TABLE IX

Influence of manganese upon the catalytic properties of the Y zeolite with 4.6% of copper.

| Catalyst | Selectivity, in CH$_3$Cl, % | Conversion in % per gramme of catalyst | Efficiency in % per gramme of catalyst |
|---|---|---|---|
| Na Cu Mn Y 4.6% Cu 2.0% Mn | 98 | 3.3 | 3.3 |
| Na Cu Y 4.6% Cu | 84 | 4.0 | 3.3 |
| Catalyst U.S. Pat. No. 4,123,389 (after 24 h) | 94 | 2.9 | 2.7 |

The results in the table hereinabove confirm that the doping of the catalyst of the present invention with manganese improves the selectivity thereof although the efficiencies or yields per gramme of doped and non doped catalysts are identical. The beneficial influence of manganese may be ascribed to its inhibiting or at least little catalytic action with respect to the reaction of total oxydizing of methyl chloride. As to the slight drop in activity induced by the addition of manganese it is comparable with that which occurs when the global exchange rate increases (see for example NaCuY with 7.6% of Cu$^{2+}$ in table III).

In respect of the advantages of the catalyst according to the invention as modified by manganese, it is found that it not only exhibits the advantages of the basic catalyst of the present invention but that moreover its steady state selectivity is higher than that of the basic catalyst of the present invention and than that of the prior art catalyst for an at least approximately or nearly same conversion rate.

What is claimed is:

1. A catalyst for the oxyhydrochlorination of methane into methyl chloride by reacting methane with hydrogen chloride and oxygen, the catalyst comprising a zeolite partially exchanged with divalent metallic Mn$^{++}$ cations and between 0.5% and 10% by weight Cu$^{++}$ cations.

2. An oxyhydrochlorination catalyst according to claim 1, wherein the zeolite is a Y-zeolite of the general formula in the initial state: Na$_{56}$(AlO$_2$)$_{56}$(SiO$_2$)$_{136}$.

3. An oxyhydrochlorination catalyst according to claim 1, wherein the exchanged zeolite comprises between about 0.5% and 7.6% by weight of Cu$^{++}$ cations.

4. An oxyhydrochlorination catalyst according to claim 3, wherein the exchanged zeolite comprises about 4.6% by weight of Cu$^{++}$ cations.

* * * * *